(12) United States Patent
Tsai (10) Patent No.: US 10,871,007 B1
(45) Date of Patent: Dec. 22, 2020

(54) FOLDING CAGE BODY

(71) Applicant: SPORT DIVERSIONS INC., Taipei (TW)

(72) Inventor: Wen-Hao Tsai, New Taipei (TW)

(73) Assignee: SPORT DIVERSIONS INC., Taipei (TW)

( * ) Notice: Subject to any disclaimer, the term of this patent is extended or adjusted under 35 U.S.C. 154(b) by 0 days.

(21) Appl. No.: 16/672,678

(22) Filed: Nov. 4, 2019

(51) Int. Cl.
*E04H 15/50* (2006.01)
(52) U.S. Cl.
CPC .................................. *E04H 15/50* (2013.01)
(58) Field of Classification Search
CPC .......... A01K 1/03; A01K 1/033; A01K 1/034; E04H 15/50; E04H 15/52; E04H 15/42; A47D 13/061; A47D 7/002; A47D 9/005; A47D 13/06
USPC .......................................... 135/131, 145, 156
See application file for complete search history.

(56) References Cited

U.S. PATENT DOCUMENTS

| 1,950,603 | A | * | 3/1934 | Fischer | A47D 13/065 |
| | | | | | 5/98.3 |
| 5,421,356 | A | * | 6/1995 | Lynch | E04H 15/50 |
| | | | | | 135/145 |
| 6,925,664 | B1 | * | 8/2005 | Twigg | A01K 1/034 |
| | | | | | 5/112 |
| 7,100,221 | B1 | * | 9/2006 | Twigg | A01K 1/034 |
| | | | | | 5/110 |
| 7,406,978 | B2 | * | 8/2008 | Mintie | B08B 15/00 |
| | | | | | 135/131 |
| 7,418,746 | B2 | * | 9/2008 | Gehr | A47D 13/063 |
| | | | | | 5/98.1 |
| 7,568,243 | B2 | * | 8/2009 | Gehr | A47D 13/063 |
| | | | | | 5/98.1 |
| 8,011,686 | B2 | * | 9/2011 | Chen | B62B 3/106 |
| | | | | | 280/651 |
| 9,428,206 | B1 | * | 8/2016 | Morton | B62B 3/022 |
| 9,561,151 | B2 | * | 2/2017 | Opsetmoen | A45B 11/00 |
| 10,040,470 | B1 | * | 8/2018 | Horowitz | B62B 5/0013 |
| 2005/0155637 | A1 | * | 7/2005 | Kim | E04H 15/50 |
| | | | | | 135/131 |
| 2006/0174928 | A1 | * | 8/2006 | Choi | E04H 15/58 |
| | | | | | 135/145 |
| 2011/0204598 | A1 | * | 8/2011 | Stevenson | B62B 3/007 |
| | | | | | 280/639 |

* cited by examiner

*Primary Examiner* — Noah Chandler Hawk
(74) *Attorney, Agent, or Firm* — Schmeiser, Olsen & Watts, LLP (57) ABSTRACT

A folding cage body includes six groups of fence members and an accommodating portion, wherein each group of the fence member includes an upright pole, an upper moveable pivotal piece, two slanting poles and two lower pivotal pieces, and the accommodating portion is provided in the fence members. The folding cage body can be freely expanded and folded and convenient and easy to move and fold.

5 Claims, 13 Drawing Sheets

FOLDING CAGE BODY

BACKGROUND OF THE INVENTION

1. Field of the Invention

The present disclosure relates to a cage body, and in particular to a folding cage body.

2. Description of the Related Art

A cage body has a variety of functions, can be used as guardrails or bed enclosures, and also can be used for storage or as a pet nest and other purposes plus a covering cloth. However, the cage body is large in size and not easy to store in a place, so a cage body that can be folded or combined comes out, and thus the occupied space of the cage body at the time of storing in a place can be reduced by expanding and folding the bracket. However, the process of expansion, folding or combination of these cages is quite complex, people often need to refer to the manual when folding or combining the cage body, so it is difficult to use.

BRIEF SUMMARY OF THE INVENTION

An objective of the present disclosure is to provide a cage body, and in particular to a folding cage body which can be expanded and folded easily for solving the problems of the traditional cage body.

To achieve at least the above objective, the present disclosure provides a folding cage body which comprises six groups of fence members and an accommodating portion. Each group of the fence member comprises an upright pole, an upper moveable pivotal piece, two slanting poles and two lower pivotal pieces. The upright poles are enclosed in a rectangle, the upright poles of each of three groups of the fence members are arranged in a length direction, and the rectangle is formed by enclosing two rows of the upright poles. The upper moveable pivotal piece and the two lower pivotal pieces are slidably provided on the upright pole. The upper moveable pivotal piece is located on the upright pole above the two lower pivotal pieces, upper ends of the two slanting poles are pivotally connected to the upper moveable pivotal piece of the fence member that belongs to the two slanting poles, lower ends of the two slanting poles of the upright pole that is located at a vertex of the rectangle are respectively connected to the lower pivotal piece which is at the below side in the two lower pivotal pieces of the adjacent upright pole along the profile of the rectangle, lower ends of the two slanting poles of the upright pole that is not located at the vertex of the rectangle are respectively connected to the lower pivotal piece which is at the upper side in the two lower pivotal pieces of the adjacent upright pole along the profile of the rectangle, the two lower pivotal pieces of the upright pole that is not located at the vertex of the rectangle are connected with each other, and the accommodating portion is provided in the fence members.

In an embodiment, each group of the fence member further comprises a separator which is fixedly provided on the upright pole and located between the upper moveable pivotal piece and the two lower pivotal pieces to separate sliding ranges of the upper moveable pivotal piece and the two lower pivotal pieces.

In an embodiment, each of two crossing slanting poles is pivotally connected with each other.

In an embodiment, the folding cage body further comprises at least one fixed fastener which is provided on the upper moveable pivotal piece of the upright pole, the fixed fastener is provided to switch between a fixed position and a free position, when the fixed fastener is in the fixed position, the upper moveable pivotal piece is fixed on the upright pole by the fixed fastener, and when the fixed fastener is in the free position, the upper moveable pivotal piece can slide relative to the upright pole.

In an embodiment, the fixed fastener is a C-type retaining ring, the upper moveable pivotal piece has a gap, and the C-type retaining ring is provided in the gap and surrounds the upright pole.

In an embodiment, each group of fence member further comprises two stops which are respectively provided at the top and bottom of the upright pole.

Therefore, the folding cage body of the invention can be freely expanded and folded, and the invention provides a cage body which is convenient and easy to move and fold, and the operation is simple and intuitive.

DETAILED DESCRIPTION OF THE INVENTION

To facilitate understanding of the object, characteristics and effects of this present disclosure, embodiments together with the attached drawings for the detailed description of the present disclosure are provided. One skilled in the art can understand the object, characteristics and effects of this present invention by the content described in the specification. It should be noted that various possible modifications and alterations to the details of the specification could be carried out by implementing or applying other different embodiments based on different views and applications without departing from the spirit of the present invention. The related technical contents of the invention will be described in detail by the embodiments. However, the disclosed contents should not be considered to limit the scope of the invention. The description is provided as follows:

As shown in FIGS. 1A to 3E and 5, the invention provides a folding cage body 100 which comprises six groups of fence members 10 and an accommodating portion 9.

Each group of the fence member 10 comprises an upright pole 2, an upper moveable pivotal piece 3, 3a, two slanting poles 4 and two lower pivotal pieces 5, 5a. These upright poles 2 are enclosed in a rectangle, the upright poles 2 of each of three groups of the fence members 10 are arranged in a length direction d, and the rectangle is formed by enclosing two rows of the upright poles 2.

As shown in FIGS. 1A to 3E and 5, the upper moveable pivotal piece 3, 3a is slidably provided on the upright pole 2, and the two lower pivotal pieces 5, 5a are fixedly provided on the upright pole 2. The upper moveable pivotal piece 3, 3a is located on the upright pole 2 above the two lower pivotal pieces 5, 5a, upper ends of the two slanting poles 4 are pivotally connected to the upper moveable pivotal piece 3, 3a of the fence member 10 that belongs to the two slanting poles 4, lower ends of the two slanting poles 4 of the upright pole 2 that is located at a vertex of the rectangle are respectively connected to the lower pivotal piece 5, 5a which is at the below side in the two lower pivotal pieces 5, 5a of the adjacent upright pole 2 along the profile of the rectangle, lower ends of the two slanting poles 4 of the upright pole 2 that is not located at the vertex of the rectangle are respectively connected to the lower pivotal piece 5 which is at the upper side in the two lower pivotal pieces 5 of the adjacent upright pole 2 along the profile of the rectangle, the two lower pivotal pieces 5a of the upright pole 2 that is not located at the vertex of the rectangle are connected with each other, the accommodating portion 9 is provided in the fence members 10, the accommodating portion 9 may be a rectangular hollow body, and may be a soft material such as cloth or plastic. With the accommodating portion 9, the folding cage body 100 can be used as a storage rack, pet nest and for other purposes, however, the present invention is not limited to herein.

In which, the fence member 10 belonging to the upright pole 2 that is located at the vertex of the rectangle has the upper moveable pivotal piece 3, and an angle between the two slanting poles 4 that are pivotally connected by the upper moveable pivotal piece 3 is nearly 90 degrees; and the fence member 10 belonging to the upright pole 2 that is not located at the vertex of the rectangle has the upper moveable pivotal piece 3a, and an angle between the two slanting poles 4 that are pivotally connected by the upper moveable pivotal piece 3a is nearly 180 degrees.

Similarly, the fence member 10 belonging to the upright pole 2 that is located at the vertex of the rectangle has the two lower pivotal pieces 5, and the two lower pivotal pieces 5 are provided at the lower end of the upright pole 2 and separated from each other at a predetermined distance; and the fence member 10 belonging to the upright pole 2 that is not located at the vertex of the rectangle has the two lower pivotal pieces 5a, and the two lower pivotal pieces 5a are connected with each other.

Next, it is described how to fold the folding cage body 100 of the invention.

Figure 1A:
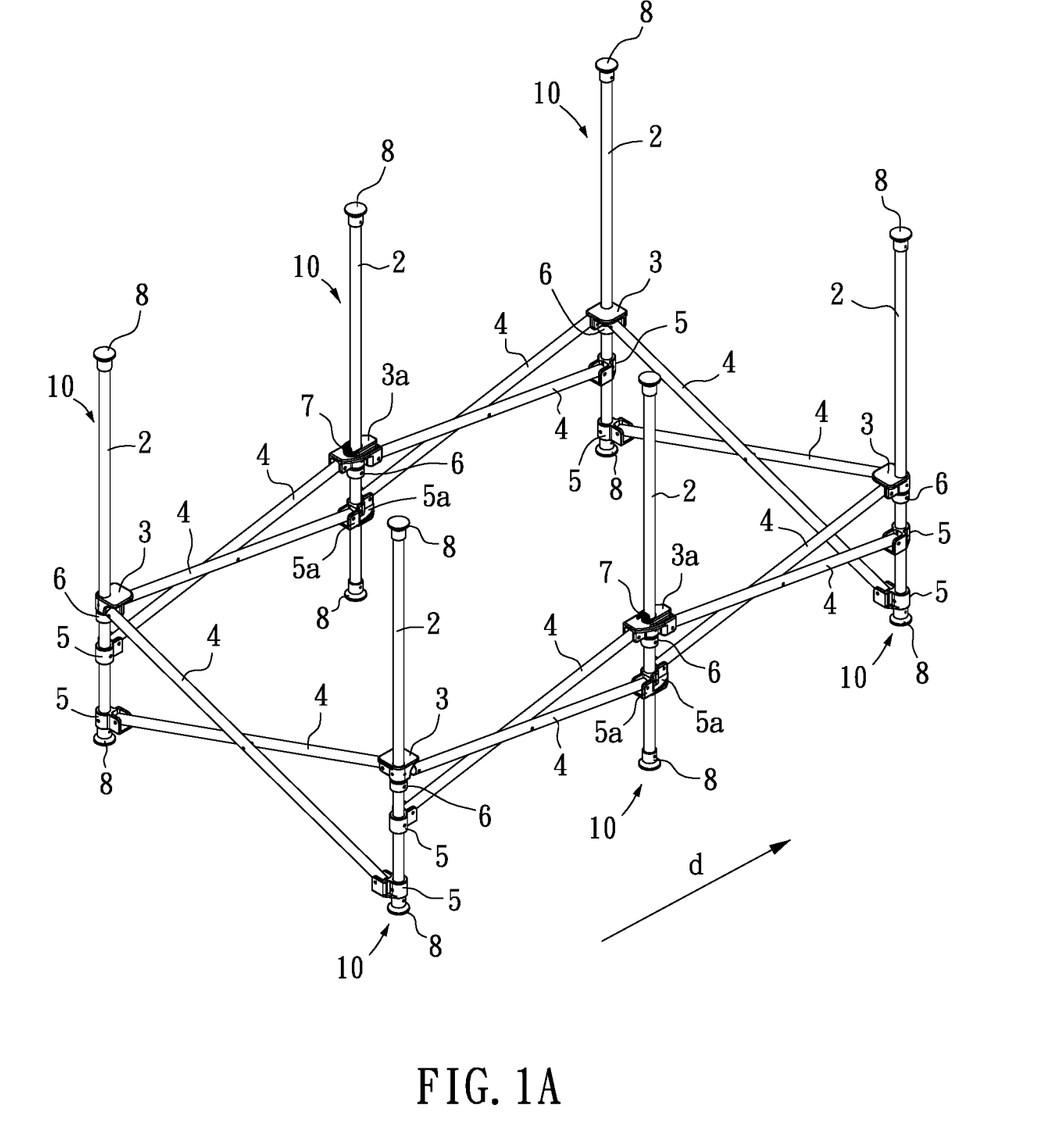
FIG. 1A is a schematic perspective view of the folding cage body according to an embodiment of the present disclosure.
Figure 1B:
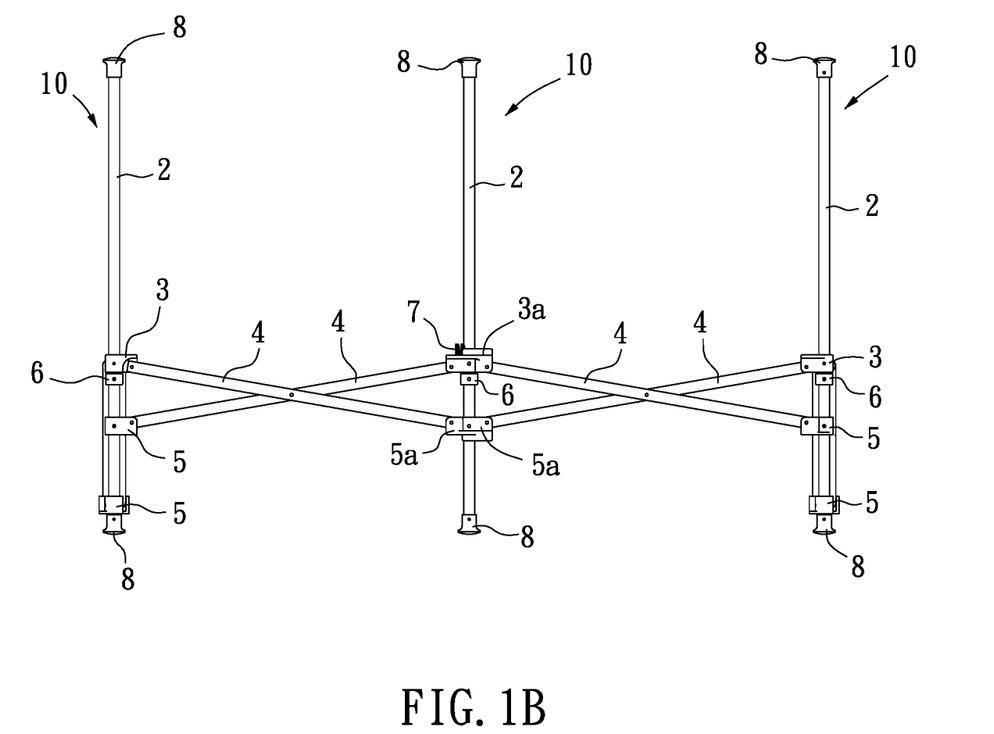
FIG. 1B is a schematic front view of the folding cage body according to the embodiment of the present disclosure.
Figure 1C:
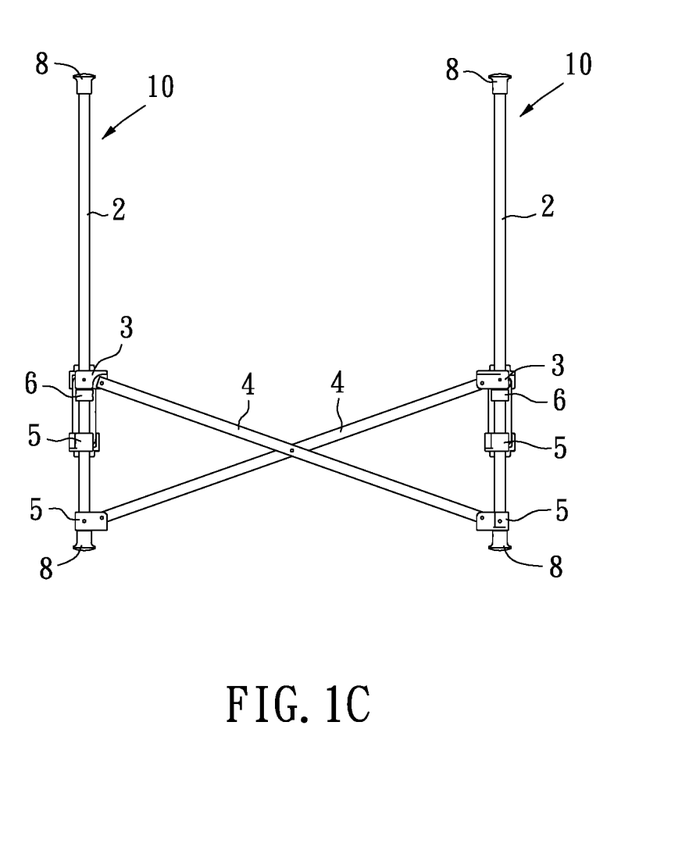
FIG. 1C is a schematic side view of the folding cage body according to the embodiment of the present disclosure.
Figure 1D:
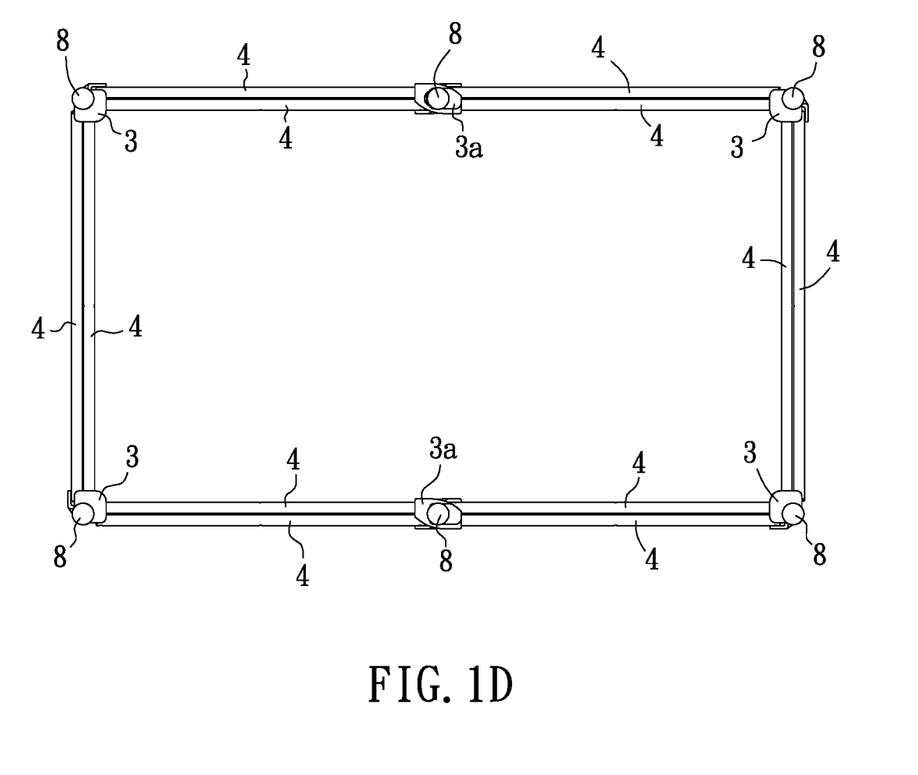
FIG. 1D is a schematic top view of the folding cage body according to the embodiment of the present disclosure.
Figure 1E:
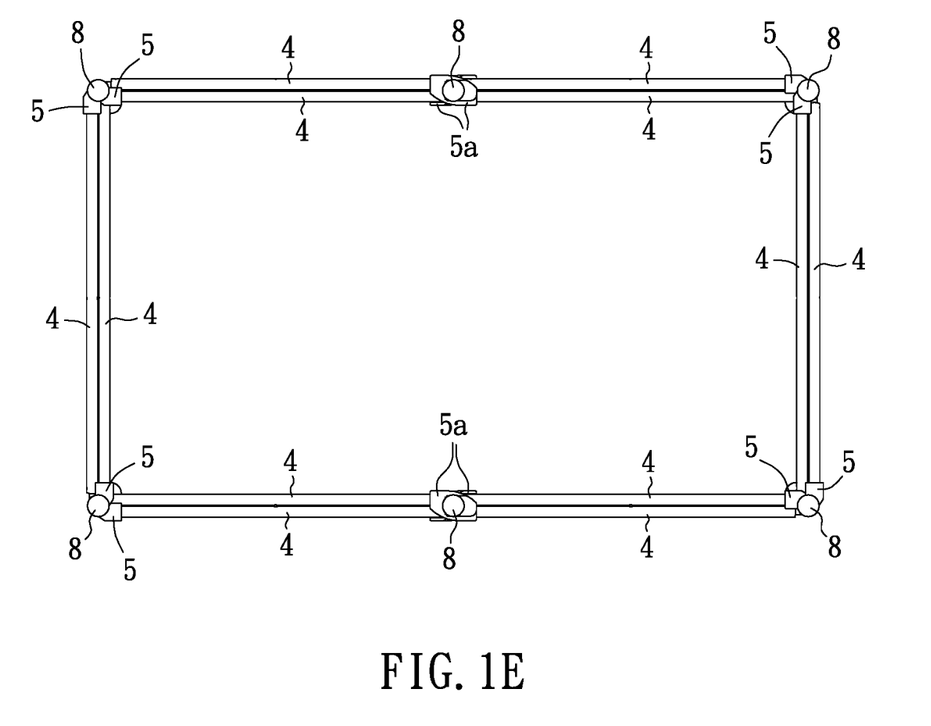
FIG. 1E is a schematic bottom view of the folding cage body according to the embodiment of the present disclosure.
Figure 2A:
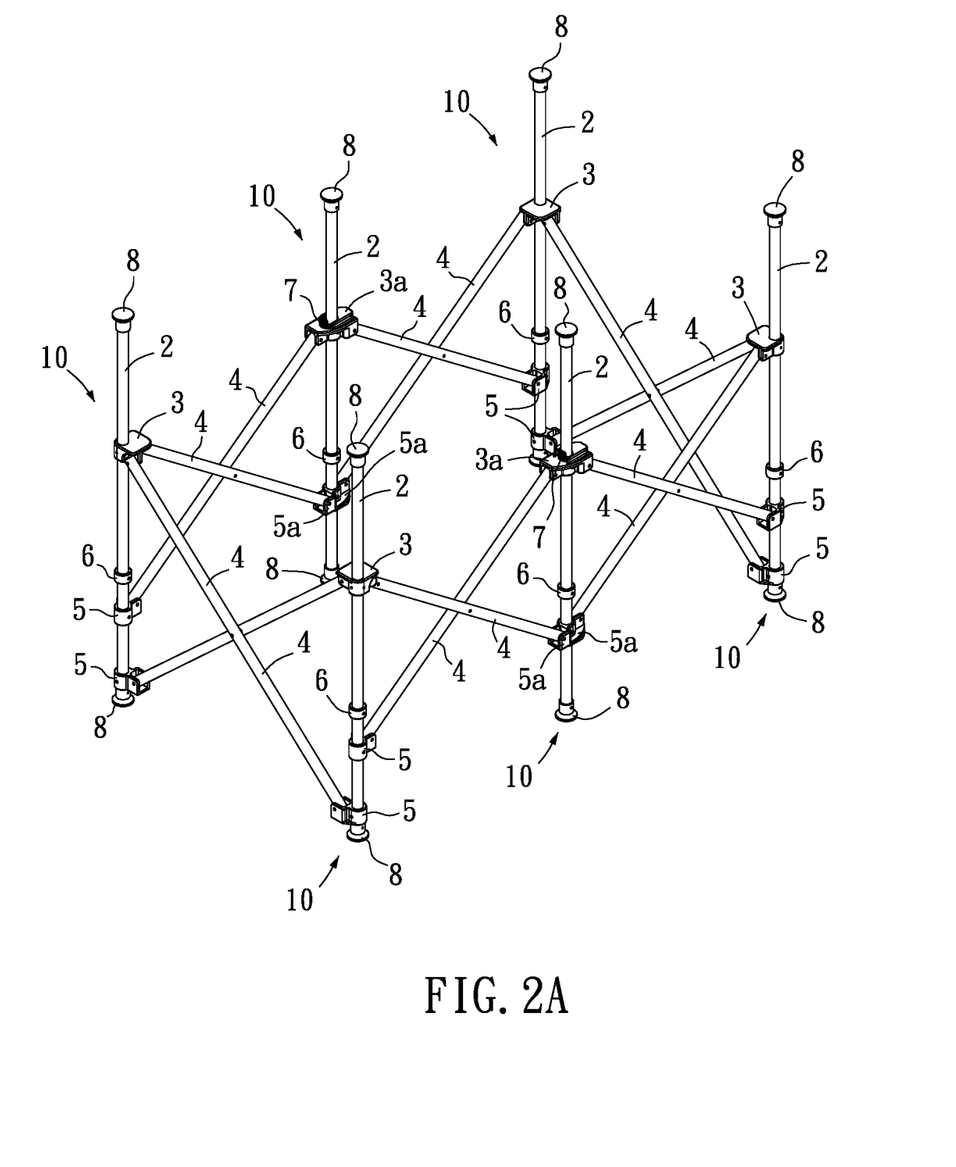
FIG. 2A is a schematic perspective view illustrating a folding process of the folding cage body according to the embodiment of the present disclosure.
Figure 2B:
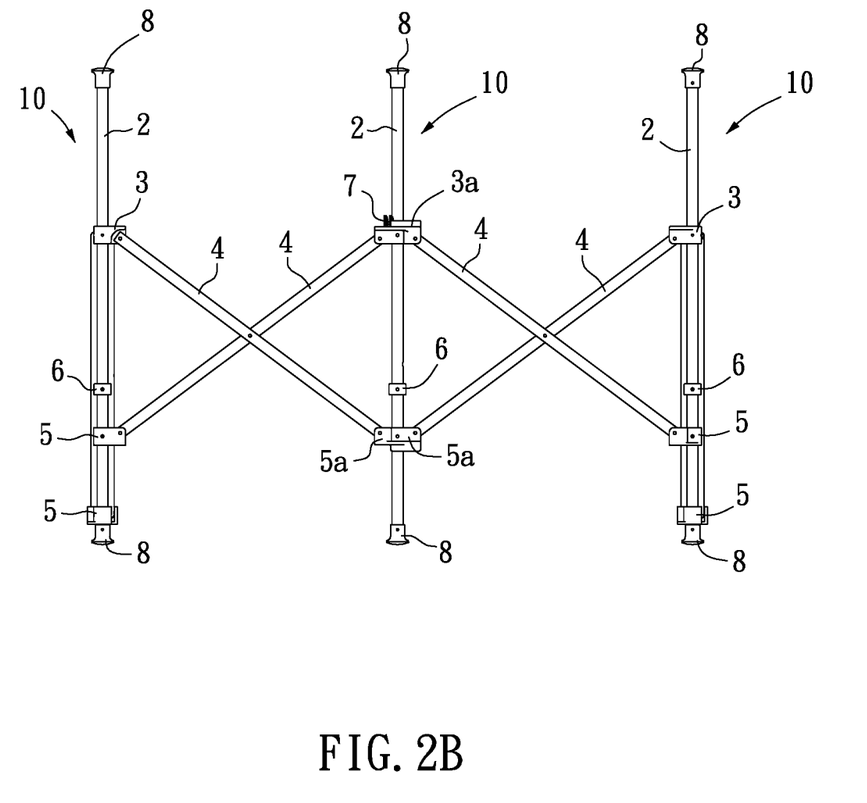
FIG. 2B is a schematic front view illustrating the folding process of the folding cage body according to the embodiment of the present disclosure.
Figure 3A:
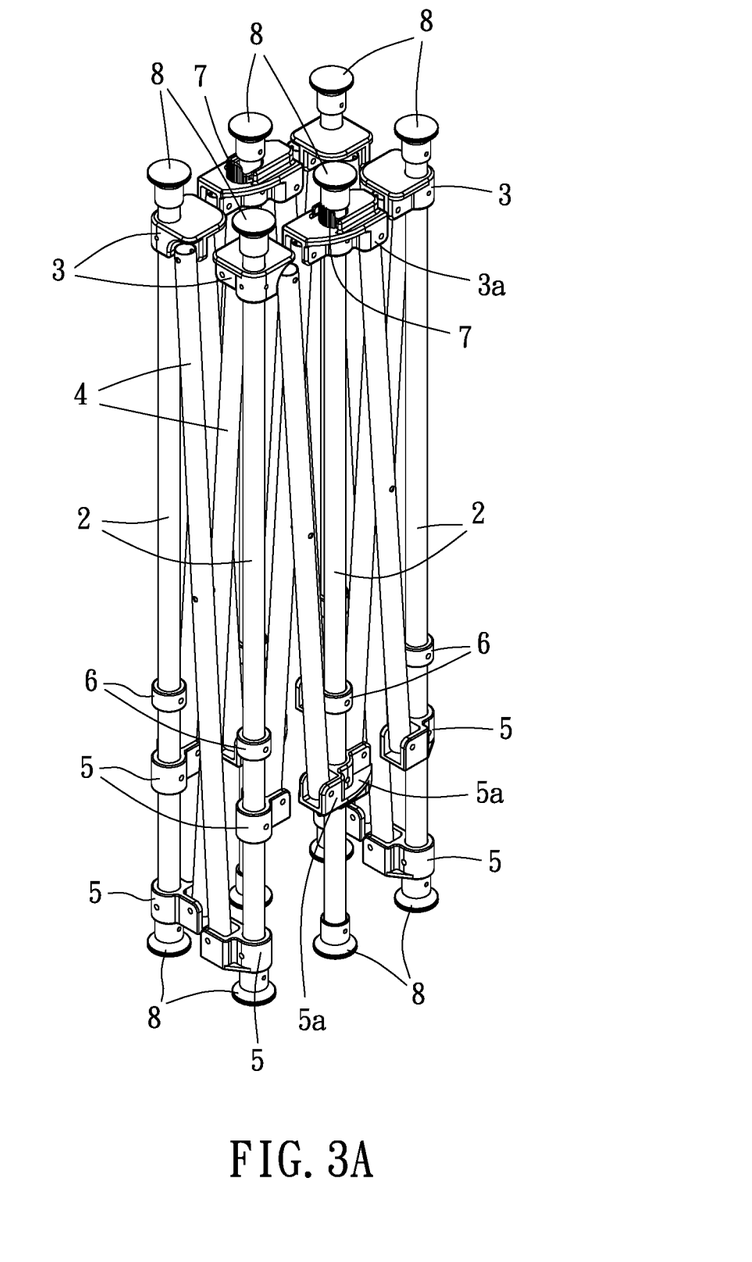
FIG. 3A is a schematic perspective view illustrating an outcome after folding of the folding cage body according to the embodiment of the present disclosure.
Figure 3B:
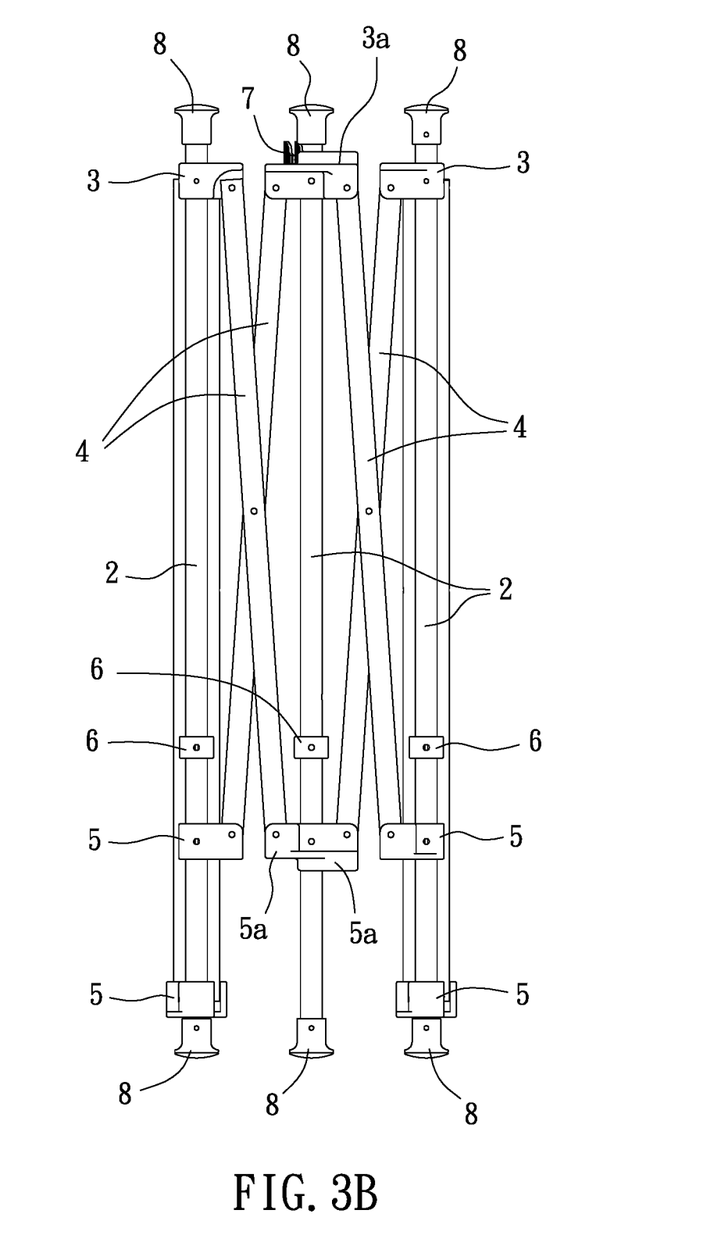
FIG. 3B is a schematic front view illustrating the outcome after folding of the folding cage body according to the embodiment of the present disclosure.
Figure 3C:
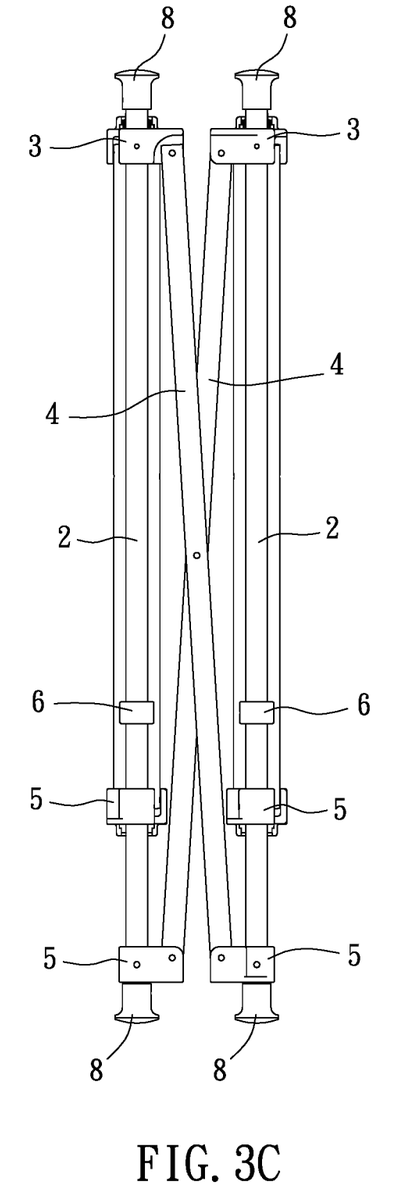
FIG. 3C is a schematic side view illustrating the outcome after folding of the folding cage body according to the embodiment of the present disclosure.
Figure 3D:
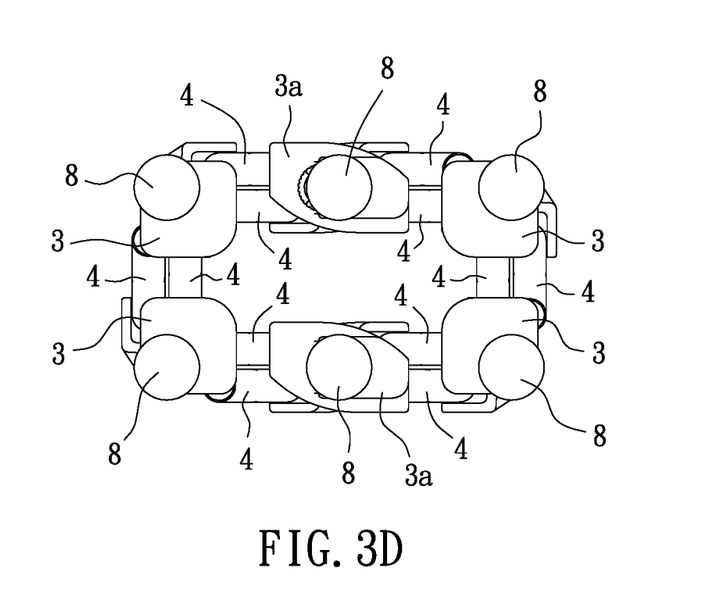
FIG. 3D is a schematic top view illustrating the outcome after folding of the folding cage body according to the embodiment of the present disclosure.
Figure 3E:
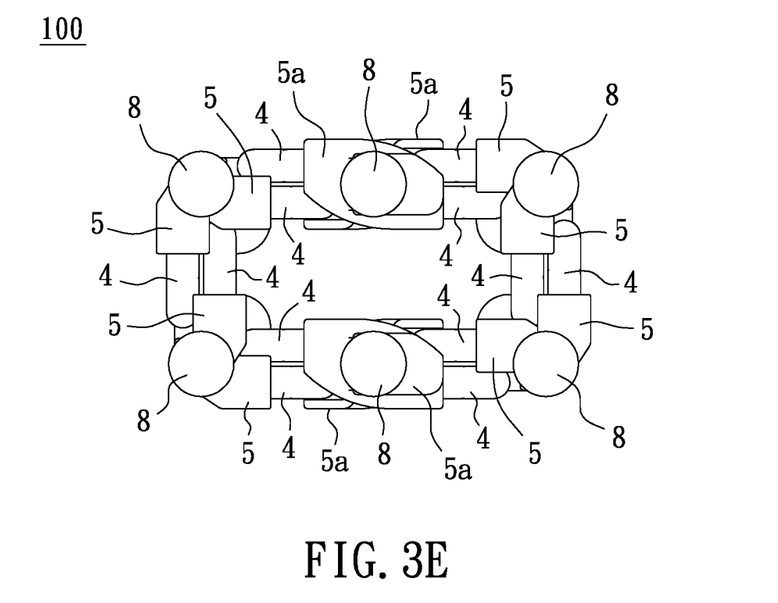
FIG. 3E is a schematic bottom view illustrating the outcome after folding of the folding cage body according to the embodiment of the present disclosure.

As shown in FIGS. 1A, 2A and 3A, and referring to FIGS. 1B, 2B and 3B, the four upright poles 2 that are located at vertexes of the rectangle are pushed inward along diagonal lines of the rectangle to push upward the slanting poles 4 for driving the upper moveable pivotal pieces 3, 3a to slide to tops of the upright poles 2, and then the slanting poles 4 that were aboriginally oblique are also folded, finally a plurality of groups of the fence members 10 are gathered and folded into a very small cluster, and the accommodating portion 9 is also folded in the fence members 10. In addition, if the four upright poles 2 that are located at the vertexes of the rectangle are pulled in the opposite directions, the folding cage body 100 of the invention can be expanded again.

Therefore, the folding cage body 100 of the invention can be freely expanded and folded, and the invention provides a cage body which is convenient and easy to move and fold, and the operation is simple and intuitive so that everyone can use easily.

Further, in an embodiment, as shown in FIG. 1A, each group of the fence member 10 comprises a separator 6 which is fixedly provided on the upright pole 2 and located between the upper moveable pivotal piece 3, 3a and the two lower pivotal pieces 5, 5a. The separator 6 limits a sliding range of the upper moveable pivotal piece 3, 3a. That is, the maximum length and width of the folding cage body 100 are limited by the position of the separator 6 on the upright pole 2.

Further, in an embodiment, as shown in FIG. 1A, each of two crossing slanting poles 4 is pivotally connected with each other to enhance the stability of the folding cage body 100.

Figure 4:
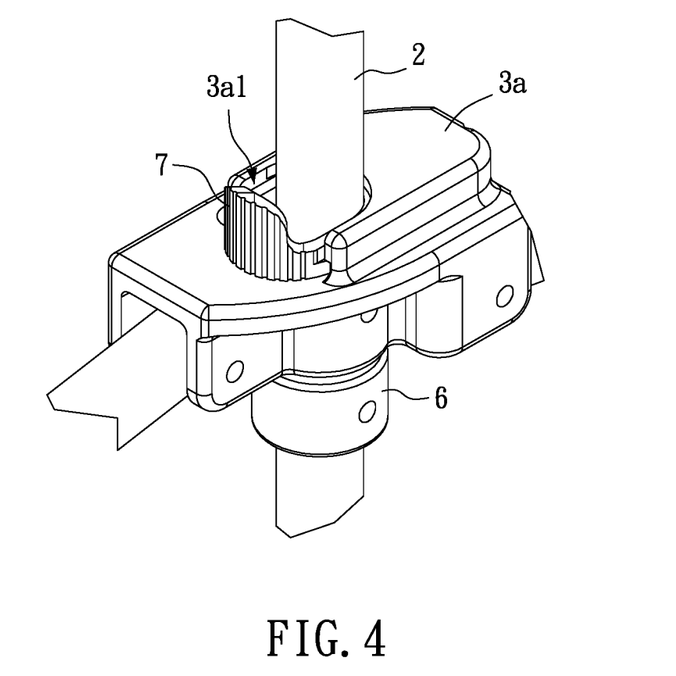
FIG. 4 is a schematic perspective view of the fixed fastener according to the embodiment of the present disclosure.
Figure 5:
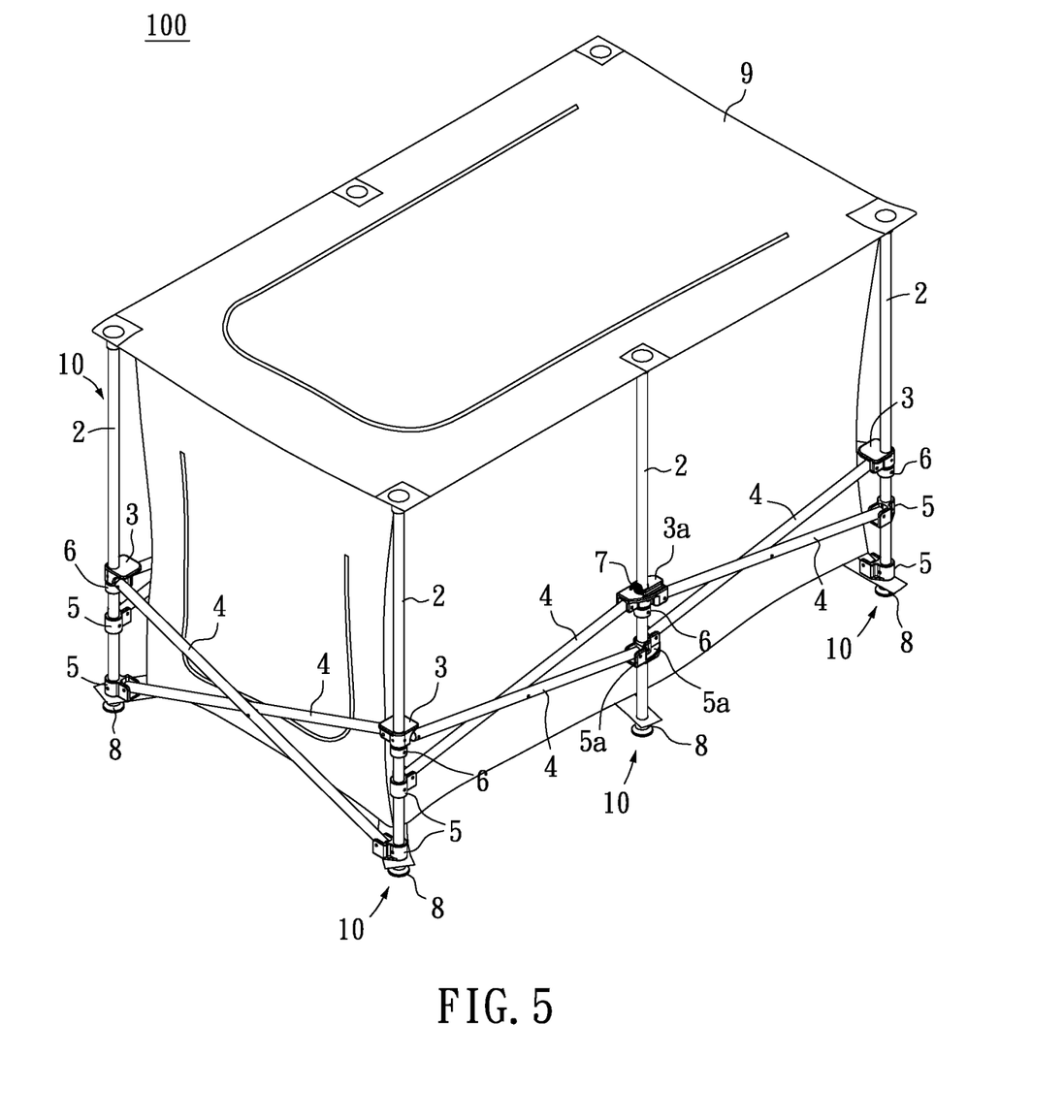
FIG. 5 is a schematic perspective view of the accommodating portion providing in the fence members according to the embodiment of the present disclosure.

Further, in an embodiment, as shown in FIGS. 1A and 4, the folding cage body 100 further comprises at least one fixed fastener 7 which is provided on the upper moveable pivotal piece 3a of the fence member 10 belonging to the upright pole 2 that is not located at the vertex of the rectangle. The fixed fastener 7 is provided to switch between a fixed position and a free position. When the fixed fastener 7 is in the fixed position, the upper moveable pivotal piece 3a is fixed on the upright pole 2 by the fixed fastener 7, and when the fixed fastener 7 is in the free position, the upper moveable pivotal piece 3a can slide relative to the upright pole 2.

Specifically, in the embodiment, the fixed fastener 7 is a C-type retaining ring, the upper moveable pivotal piece 3a has a gap 3a1, and the C-type retaining ring is provided in the gap 3a1 and surrounds the upright pole 2. When the C-type retaining ring is pressed, the C-type retaining ring is in the fixed position to firm the upright pole 2 and the upper moveable pivotal piece 3a cannot slide relative to the upright pole 2, and when the C-type retaining ring is pulled out, the C-type retaining ring is in the free position to release the upright pole 2 and the upper moveable pivotal piece 3a can slide relative to the upright pole 2. Therefore, when the folding cage body 100 expands or folds, the position between each upright pole 2 can be fixed by the fixed fastener 7. However, the invention is not limited to herein, and the fixed fastener 7 may be other conventional forms.

Further, in an embodiment, as shown in FIG. 1A, each group of fence member 10 further comprises two stops 8 which are respectively provided at the top and bottom of the upright pole 2. Therefore, the upright pole 2 can be stably provided on the ground and the sliding range of the upper moveable pivotal piece 3, 3a can be limited.

While the present disclosure has been described by means of specific embodiments, numerous modifications and variations could be made thereto by those skilled in the art without departing from the scope and spirit of the present disclosure set forth in the claims. The above description is merely embodiments of the invention, and it should not be considered to limit the scope of the invention. It should be noted that all changes and substitutions which come within the meaning and range of equivalency of the embodiments are intended to be embraced in the scope of the invention. Therefore, the scope of the invention is defined by the claims.

What is claimed is:

1. A folding cage body, comprising:
    an accommodating portion; and
    six groups of fence members, wherein the accommodating portion is provided in the fence members, and each group of the fence member comprises:
        an upright pole, wherein the upright pole is enclosed in a rectangle, the upright pole of each of three groups of the fence members are arranged in a horizontal direction, and the rectangle is formed by enclosing two rows of upright poles;
        an upper moveable pivotal piece, wherein the upper moveable pivotal piece is slidably provided on the upright pole;
        two slanting poles, wherein upper ends of the two slanting poles are pivotally connected to the upper moveable pivotal piece of the fence member that belongs to the two slanting poles;
        two lower pivotal pieces, wherein the two lower pivotal pieces are fixedly provided on the upright pole; and
        a separator which is fixedly provided on the upright pole and located between the upper moveable pivotal piece and the two lower pivotal pieces to limit a sliding range of the upper moveable pivotal piece,
    wherein the upper moveable pivotal piece is located on the upright pole above the two lower pivotal pieces,
    lower ends of the two slanting poles of the upright pole that is located at a vertex of the rectangle are respectively connected to the lower pivotal piece which is at the below side in the two lower pivotal pieces of the adjacent upright pole along the profile of the rectangle,
    lower ends of the two slanting poles of the upright pole that are not located at the vertex of the rectangle are respectively connected to the lower pivotal piece which is at the upper side in the two lower pivotal pieces of the adjacent upright pole along the profile of the rectangle,
    wherein the two lower pivotal pieces of the upright pole that are not located at the vertex of the rectangle are connected with each other.

2. The folding cage body according to claim 1, wherein each of two crossing slanting poles is pivotally connected with each other.

3. The folding cage body according to claim 1, further comprising at least one fixed fastener which is provided on the upper moveable pivotal piece of the upright pole, the fixed fastener is provided to switch between a fixed position and a free position, when the fixed fastener is in the fixed position, the upper moveable pivotal piece is fixed on the upright pole by the fixed fastener, and when the fixed fastener is in the free position, the upper moveable pivotal piece can slide relative to the upright pole.

4. The folding cage body according to claim 3, wherein the fixed fastener is a C-type retaining ring, the upper moveable pivotal piece has a gap, and the C-type retaining ring is provided in the gap and surrounds the upright pole.

5. The folding cage body according to claim 1, wherein each group of fence member further comprises two stops which are respectively provided at the top and bottom of the upright pole.

* * * * *